United States Patent
Darapu

(10) Patent No.: US 12,272,451 B2
(45) Date of Patent: Apr. 8, 2025

(54) WIRELESS CHARGING OF MEDICAL DEVICES

(71) Applicant: Medtronic, Inc., Minneapolis, MN (US)

(72) Inventor: Mahipal Reddy Darapu, Hyderabad (IN)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 17/937,054

(22) Filed: Sep. 30, 2022

(65) Prior Publication Data

US 2023/0113606 A1    Apr. 13, 2023

Related U.S. Application Data

(60) Provisional application No. 63/254,626, filed on Oct. 12, 2021.

(51) Int. Cl.
*G16H 40/40* (2018.01)
*G16H 40/63* (2018.01)
*H02J 7/00* (2006.01)

(52) U.S. Cl.
CPC ............. *G16H 40/40* (2018.01); *G16H 40/63* (2018.01); *H02J 7/0045* (2013.01)

(58) Field of Classification Search
CPC ........ G16H 40/40; G16H 40/63; G16H 40/67; H02J 7/0045
See application file for complete search history.

(56) References Cited

U.S. PATENT DOCUMENTS

| | | | |
|---|---|---|---|
| 8,649,757 B2 | 2/2014 | Roberts et al. | |
| 9,111,189 B2 | 8/2015 | Scalisi et al. | |
| 9,427,160 B2 | 8/2016 | Proud et al. | |
| 9,673,665 B2 | 6/2017 | Zeine et al. | |
| 10,418,863 B1 | 9/2019 | Jadidian et al. | |
| 10,615,647 B2 | 4/2020 | Johnston et al. | |
| 10,826,316 B2 | 11/2020 | Lin et al. | |
| 11,701,976 B2 * | 7/2023 | Waters | B60L 53/60 320/108 |
| 12,014,816 B2 * | 6/2024 | Knickerbocker | A61B 5/0022 |

(Continued)

FOREIGN PATENT DOCUMENTS

WO    2019/195208 A1    10/2019

OTHER PUBLICATIONS

Fan et al., "Towards Flexible Wireless Charging for Medical Implants Using Distributed Antenna System," Association for Computing Machinery, DOI: 10.1145/3372224.3380899, Feb. 2020, 15 pp.

(Continued)

*Primary Examiner* — Eliza A Lam
(74) *Attorney, Agent, or Firm* — Shumaker & Sieffert, P.A.

(57) ABSTRACT

This disclosure is directed to devices, systems, and techniques for wirelessly charging a medical device. A charging device may receive a request to wirelessly charge a medical device. The charging device may, in response to receiving the request, physically move within wireless charging range of the medical device. The charging device may, in response to determining that the charging device is within the wireless charging range of the medical device, wirelessly transmit power to the medical device to wirelessly charge the medical device.

20 Claims, 5 Drawing Sheets

(56) References Cited

U.S. PATENT DOCUMENTS

| | | | |
|---|---|---|---|
| 2012/0197351 A1 | 8/2012 | Olson et al. | |
| 2019/0184842 A1 | 6/2019 | Waters | |
| 2019/0217737 A1* | 7/2019 | Lotfy | G06Q 10/02 |
| 2019/0247669 A1 | 8/2019 | Nielsen et al. | |
| 2019/0379232 A1 | 12/2019 | Lemdiasov et al. | |
| 2020/0031248 A1* | 1/2020 | Kwak | G05D 1/0231 |
| 2020/0082352 A1* | 3/2020 | Liu | B60L 53/63 |
| 2020/0177026 A1 | 6/2020 | Sosinov et al. | |

OTHER PUBLICATIONS

International Search Report and Written Opinion of International Application No. PCT/US2022/077475 dated Dec. 22, 2022, 12 pp.

Khan et al., "Wireless Power Transfer Techniques for Implantable Medical Devices: A Review," MDPI, Sensors, vol. 20, No. 3487, DOI: 10.3390/s20123487, Jun. 2020, 58 pp.

Lu et al., "Wireless Charging Technologies: Fundamentals, Standards, and Network Applications," IEEE Communications Surveys and Tutorials, to Appear, arXiv: 1509.00940v2, Nov. 2015, 40 pp.

Rajasekaran et al., "Autonomous Monitoring in Healthcare Environment: Reward-based Energy Charging Mechanism for IoMT Wireless Sensing Nodes," Research Gate, DOI: 10.13140/RG.2.22287.641168, Jan. 2019, 34 pp.

* cited by examiner

WIRELESS CHARGING OF MEDICAL DEVICES

This application claims the benefit of U.S. Provisional Application Ser. No. 63/254,626, filed Oct. 12, 2021, which is entitled "WIRELESS CHARGING OF MEDICAL DEVICES" and is incorporated by reference herein in its entirety.

TECHNICAL FIELD

The disclosure relates to wireless charging of medical devices worn on or implanted in a patient.

BACKGROUND

A medical device that is worn or implanted in a patient, such as an implantable medical device (IMD), may include a battery that may require periodic recharging. To support recharging of such a battery, the medical device may include a port, socket, or other means for attaching a wire from a power source to the medical device or may use near-field induction in order to recharge the battery of the medical device.

SUMMARY

In general, the disclosure is directed to devices, systems, and techniques for wireless charging of medical devices implanted in patients or worn on the bodies of patients. A charging device may be able to receive, via wireless communications, a request to wirelessly charge a medical device implanted in or worn by a patient in a facility, such as a hospital or a clinic. The charging device may be a robotic device that includes mechanisms such as wheels, robotic legs, and the like, to physically move the charging device to different locations within the facility. The charging device may, in response to receiving the request to wirelessly charge the medical device, physically move the charging device across the facility to within wireless charging range of the medical device. When the charging device is within wireless charging range of the medical device, the charging device may wirelessly transmit power to the medical device to perform wireless charging of the medical device.

The techniques of this disclosure may provide one or more advantages. Performing wireless charging of a medical device may be more user friendly compared with having to plug a wire from a power source into a port of the medical device in order to charge the medical device, and may prevent wear and tear to such a port that may be caused by plugging and unplugging wires into and out of the socket, thereby increasing the reliability and longevity of medical devices. Wireless charging the medical device of a patient may also increase the freedom of movement of a patient as the patient's medical device is being recharged, such as by preventing the patient from being tethered to a power source, such as an electrical socket on a wall or a fixed near-field inductive charger in order to charge the medical device.

In one example, a method includes receiving, by processing circuitry of a charging device, a request to wirelessly charge a medical device; in response to receiving the request, physically moving, by the charging device, within wireless charging range of the medical device; and in response to determining that the charging device is within the wireless charging range of the medical device, wirelessly transmitting, by power transmission circuitry of the charging device, power to the medical device to wirelessly charge the medical device.

In another example, a charging device configured to wirelessly transmit power, wherein the charging device comprises: movement mechanism configured to physically move the charging device; communication circuitry configured for wireless communication; power transmission circuitry configured to wirelessly transmit power; and processing circuitry electrically coupled to the movement mechanism, the communication circuitry, and the power transmission circuitry, wherein the processing circuitry is configured to: receive, via the communication circuitry, a request to wirelessly charge a medical device; and in response to receiving the request, cause the movement mechanism to physically move the charging device within wireless charging range of the medical device; wherein the power transmission circuitry is further configured to, in response to determining that the charging device is within the wireless charging range of the medical device, wirelessly transmit power to the medical device to wirelessly charge the medical device.

In another example, a non-transitory computer-readable storage medium comprising program instructions that, when executed by processing circuitry of a charging device, cause the processing circuitry to: receive, a request to wirelessly charge a medical device; in response to receiving the request, cause the charging device to move within wireless charging range of the medical device; and in response to determining that the charging device is within the wireless charging range of the medical device, cause power transmission circuitry of the charging device to wirelessly transmit power to the medical device to wirelessly charge the medical device.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
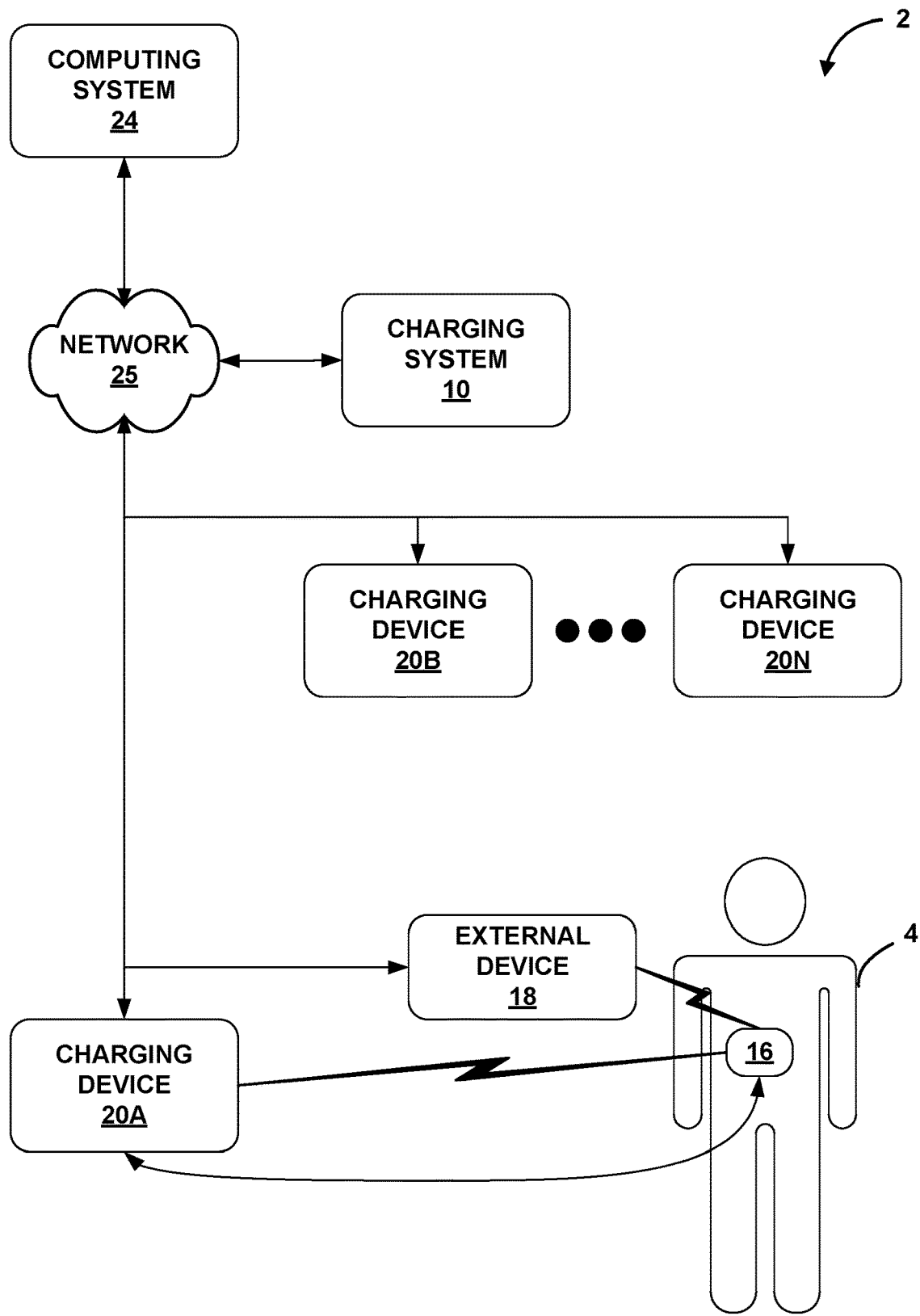
FIG. 1 illustrates the environment of an example medical device system in conjunction with a patient, in accordance with one or more techniques of this disclosure.

FIG. 1 illustrates the environment of an example medical device system 2 in conjunction with a patient 4, in accordance with one or more techniques of this disclosure. The example techniques may be used with medical device 16, which may be in wireless communication with external device 18 and with one or more of charging devices 20A-20N ("charging devices 20"). Charging devices 20 configured to wirelessly transmit electrical energy to medical devices, such as medical devices 16, to perform wireless charging the power sources (e.g., batteries) of the medical devices. Charging devices 20 and external device 18 may connect to network 25 to communicate with charging system 10 and computing system 24.

In some examples, medical device 16 is an implantable medical device (IMD) that is implanted in patient 4. In some examples, medical device 16 takes the form of a LINQ™ Insertable Cardiac Monitor (ICM), available from Medtronic plc, of Dublin, Ireland. Other examples of medical device 16 may include implantable cardioverter defibrillators (ICDs), pacemakers, cardiac resynchronization therapy devices (CRT-Ds), spinal cord stimulation (SCS) devices, deep brain stimulation (DBS) devices, left ventricular assist devices (LVADs), implantable sensors, orthopedic devices, or drug pumps, as examples. In some examples, medical device 16 may be a wearable medical device worn by patient 4, such as an insulin pump, a continuous glucose monitor, and the like.

External device 18 is configured to wirelessly communicate with medical device 16 as needed to provide or retrieve information. In some examples, external device 18 acts as an external programming device, e.g., medical device programmer, for medical device 16. External device 18 is an external computing device that a user, e.g., the clinician and/or patient 4, may use to communicate with medical device 16. For example, external device 18 may be a clinician programmer that the clinician uses to communicate with medical device 16 and update one or more settings of medical device 16. Additionally, or alternatively, external device 18 may be a patient programmer that allows patient 4 to control certain operations of medical device 16 and/or view and modify one or more operational parameter values of medical device 16. The clinician programmer may include more programming features than the patient programmer.

External device 18 may be a hand-held computing device with a display viewable by the user and an interface for providing input to external device 18 (i.e., a user input mechanism). For example, external device 18 may include a small display screen (e.g., a liquid crystal display (LCD) or a light emitting diode (LED) display) that presents information to the user. In addition, external device 18 may include a touch screen display, keypad, buttons, a peripheral pointing device, voice activation, or another input mechanism that allows the user to navigate through the user interface of external device 18 and provide input. If external device 18 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 18 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device. In some examples, a wireless adapter coupled to the computing device enables external device 18 to establish a wireless communications link, such as a Bluetooth Low Energy connection, between the computing device and medical device 16.

When external device 18 is configured for use by the clinician, external device 18 may be used to transmit instructions to medical device 16. Example instructions may include requests to set electrode combinations for sensing and any other information that may be useful for programming into medical device 16. The clinician may also configure and store operational parameters for medical device 16 within medical device 16 with the aid of external device 18. In some examples, external device 18 assists the clinician in the configuration of medical device 16 by providing a system for identifying potentially beneficial operational parameter values.

Whether external device 18 is configured for clinician or patient use, external device 18 is configured to communicate with medical device 16 via wireless communication. External device 18, for example, may communicate via near-field communication technologies (e.g., inductive coupling, NFC or other communication technologies operable at ranges less than 10-20 cm) and far-field communication technologies (e.g., RF telemetry according to the 802.11, Bluetooth, or Bluetooth Low Energy specification sets, or other communication technologies operable at ranges greater than near-field communication technologies).

External device 18 may also be configured to communicate with computing system 24, charging devices 20, and charging system 10 via network 25. Computing system 24 may comprise computing devices configured to allow a user to interact with medical device 16, or data collected from medical device 16, via network 25. For example, computing system 24 may include one or more handheld computing devices, computer workstations, servers or other networked computing devices. In some examples, computing system 24, network 25, and external device 18 may be implemented by the Medtronic Carelink™ Network or other patient monitoring system.

Charging system 10 may comprise computing devices configured to communicate with, monitor and control charging devices 20, including sending one or more commands to charging devices 20. For example, charging system 10 may include one or more handheld computing devices, computer workstations, servers or other networked computing devices.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers, and may thus form part of a large-scale public network infrastructure, e.g., the Internet. Network 25 may provide computing devices, such as external device 18, computing system 24, medical device 16, charging system 10, and charging devices 20 access to the Internet, and may provide a communication framework that allows the computing devices to communicate with one another. In some examples, network 25 may be a private network that provides a communication framework that allows charging system 10, charging devices 20, computing system 24, medical device 16, and/or external device 18 to communicate with one another but isolates one or more of charging system 10, charging devices 20, computing system 24, medical device 16, or external device 18 from devices external to network 25 for security purposes. In some examples, the communications between computing system 24, medical device 16, and external device 18, charging devices 20, and charging system 10 are encrypted.

Charging devices 20 are devices configured to perform wireless charging of medical devices worn by or implanted in patients, such as medical device 16 being worn by or implanted in patient 4. In some examples, charging devices 20 may be computing devices, robotic devices, and the like that includes power transmission circuitry to wirelessly transmit electrical energy, electrical power, electromagnetic energy and/or electronic data signals to medical devices, such as medical device 16, to perform wireless charging of power sources (e.g., batteries) of the medical devices. Charging devices 20 may be able to wirelessly transmit power at distances from a few (e.g., three) centimeters to a few (e.g., five or more) meters to the medical devices. Medical devices, such as medical device 16, may be configured to receive the energy transmitted by charging devices 20 and to charge the power sources of the medical devices using the transmitted energy received from charging devices 20.

In the example of FIG. 1, charging device 20A may be configured to wirelessly transmit energy to medical device 16 and/or inductively couple to medical device 16 to wirelessly charge the battery or other rechargeable power source of medical device 16 in response to receiving a request to wirelessly charge medical device 16. In some examples, the request to wirelessly charge medical device 16 may be user input received by charging device 20A, such as voice input (e.g., a voice command to wirelessly charge medical device 16), touch-based input at a touchscreen operably coupled to charging device 20A, and the like. In some examples, the request to wirelessly charge medical device 16 may be a request sent by charging system 10 via network 25 to charging device 20A, Medical device 16 may be configured to broadcast advertisements, such as via wireless communications (e.g., Wi-Fi), that are requests for wireless charging by a charging device. In some examples, medical device 16 may broadcast such advertisements via external device 18, so that medical device 16 may communicate the advertisements to external device 18, and external device may broadcast the advertisements, such as via wireless communications (e.g., Wi-Fi). Examples of such advertisements may be in the form of data that is wirelessly transmitted by medical device 16, audible alerts outputted by medical device 16, visual alerts outputted by medical device 16, and the like.

Medical device 16 may be configured to determine, based on factors such as the remaining battery life and/or capacity of the battery of medical device 16, the discharge rate of the battery, a predicted future discharge rate of the battery, and/or any other suitable information, to determine whether a battery of medical device 16 should be recharged. Medical device 16 may, in response to determining that a battery of medical device should be recharged, broadcast advertisements that are requests for wireless charging of medical device 16's battery by a charging device. For example, if the remaining battery life and/or capacity of the battery of medical device 16 is less than a specified threshold, and/or if the discharge rate of the battery is greater than a specified threshold, medical device 16 may determine that the battery should be recharged and may broadcast advertisements that are requests for wireless charging by a charging device.

Charging device 20A may be configured to receive an advertisement broadcasted by medical device 16. Because charging device 20A may not be within range of medical device 16 to be able to wirelessly charge medical device 16, charging device 20A may, in response to receiving the advertisement from medical device 16, determine the physical location of medical device 16 using any suitable techniques.

Charging device 20A may be configured to determine, based on the physical location of medical device 16, whether medical device 16 is within range of being wirelessly charged by charging device 20A. If charging device 20A determines that medical device 16 is not within range of being wirelessly charged by charging device 20A, charging device 20A may physically move (i.e., travel) to be within wireless charging range of medical device 16. For example, charging device 20A may be part of a vehicle or other mechanical device that includes components and/or mechanisms such as wheels, mechanical legs, skates, treads, and the like that enables charging device 20A to physically move and change locations.

Charging device 20A may be configured to determine the location of medical device 16 relative to charging device 20A and to determine one or more paths charging device 20A may take to move within wireless charging range of medical device 16. In examples where charging device 20A and medical device 16 are physically located in the same facility, such as a hospital or a clinic, charging device 20A may be configured to receive the floor plan of the facility from charging system 10 and/or computing system 24. Charging device 20A may therefore be configured to determine, based on the physical location of medical device 16 and the floor plan of the facility, a path that charging device 20A may follow to navigate the facility in order to physically move within range of medical device 16 for the purposes of wirelessly charging medical device 16.

In some examples, if medical device 16 includes a location sensor, such as a Global Positioning System (GPS) sensor, medical device 16 may be configured to send location information generated by the GPS sensor to charging device 20A, either via direct wireless communications or via network 25. In some examples, if medical device 16 does not include a location sensor, external device 18 may include a location sensor, such as a GPS sensor, and external device 18 may be configured to send location information generated by the GPS sensor of external device 18 to charging device 20A, either via direct wireless communications or via network 25. Charging device 20A may be configured to determine, based on the location information associated with medical device 16 and/or external device 18, the location of medical device 16 within the facility, and may navigate, based on the floor plans of the facility, the facility to physically move within wireless charging range of medical device 16.

In some examples, charging device 20A and/or external device 18 may be configured to use information derived from Bluetooth beacons, Wi-Fi triangulation, Bluetooth Low Energy geofencing, and the like, to determine the physical location of medical device 16 in the facility, such as the room or area of the facility where charging device 20A is located, and may send information regarding the physical location of medical device 16 in the facility to charging device 20A, either via direct wireless communications or via network 25. Medical device 16 may be configured to determine, based on the location information associated with medical device 16 and/or external device 18, the location of medical device 16 within the facility, and may navigate, based on the floor plans of the facility, the facility to physically move within wireless charging range of medical device 16.

In some examples, charging device 20A may include one or more image sensors (e.g., one or more cameras), one or more laser imaging, detection, and ranging (LIDAR) sensors, and the like that may assist charging device 20A in navigating a facility based on floor plans of the facility to reach medical device 16. For example, charging device 20A may be configured to use such image sensors and/or LIDAR sensors to sense and navigate around obstacles in order to physically move through the facility towards wireless charging range of medical device 16.

When charging device 20A is within wireless charging range of medical device 16, charging device 20A may be configured to, in response to receiving the advertisement from medical device 16, establish a secure communication session with medical device 16. Charging device 20A and medical device 16 may establish a secure communication session using any suitable technique. In some examples, charging device 20A and medical device 16 may encrypt communications between charging device 20A and medical device 16. For example, charging device 20A and medical device 16 may exchange encryption keys to encrypt communications between charging device 20A and medical device 16. In some examples, charging device 20A may send an identity associated with charging device 20A to medical device 16, and medical device 16 may determine, based on the identity associated with charging device 20A, a public encryption key for encrypting communications sent to charging device 20A. Similarly, medical device 16 may send an identity associated with medical device 16 to charging device 20A, and charging device 20A may determine, based on the identity associated with medical device 16, a public encryption key for encrypting communications sent to medical device 16

Charging device 20A and medical device 16 may be configured to communicate one or more parameters associated with wirelessly charging medical device 16. For example, medical device 16 may send, to charging device 20A, information regarding the power requirements of medical device 16, such as the desired level of power (e.g., in Watts) to transmit from charging device 20A to medical device 16, the duration of the wireless charging, and the like. Charging device 20A may therefore transmit power to medical device 16 according to the one or more parameters to re-charge the battery of medical device 16.

In some examples, one or more medical devices other than medical device 16 may also be within wireless charging range of charging device 20A. As such, before charging device 20A starts to transmit power to medical device 16 to re-charge the battery of medical device 16, these one or more medical devices within wireless charging range of charging device 20A may turn off their power receiving circuitry or may turn completely off to avoid receiving the power transmitted by charging device 20A.

In some example, medical device 16 may be configured to transmit, via wireless communication to one or more medical devices that are physically nearby medical device 16 and within wireless charging range of charging device 20A, an indication that medical device 16 is about to begin receiving power transmitted by charging device 20A to enable the one or more medical devices to turn off their power receiving circuitry. In some examples, charging device 20A may be configured to transmit, via wireless communication to one or more medical devices other than medical device 16 that are within wireless charging range of charging device 20A, an indication that medical device 16 is about to begin receiving power transmitted by charging device 20A to enable the one or more medical devices to turn off their power receiving circuitry.

For example, charging device 20A may broadcast an indication that that medical device 16 is about to begin receiving power transmitted by charging device 20A that can be received by all medical devices within wireless charging range of charger device 20A. The indication that that medical device 16 is about to begin receiving power transmitted by charging device 20A may include the identity of medical device 16 that is to be charged by charging device 20A. Each respective medical device that receives the indication that that medical device 16 is about to begin receiving power transmitted by charging device 20A may determine, based on the identity of medical device 16 included in the received indication, whether the respective medical device is medical device 16 that is about to be charged by charging device 20A. Each respective medical device may, in response to determining that the respective medical device is not medical device 16, turn off their power receiving circuitry.

In some examples, charging device 20A may be able to wirelessly charge multiple medical devices at the same time (e.g., wirelessly charge a first medical device while wirelessly charging a second medical device). To support wireless charging of multiple medical devices at the same time, charging device 20A may include power transmission circuitry that may be able to transmit power to two or more medical devices at the same time at the same or different levels of power. That is, the power transmission circuitry of charging device 20A may be able to transmit power at a first desired power level to a first device while transmitting power at a second desired power level to a second device, where the first desired power level is different (e.g., higher or lower) than the second desired power level.

In some examples, charging device 20A may receive advertisements that are requests for wireless charging by a charging device from multiple medical devices and may determine a prioritization of the multiple medical devices. For example, if charging device 20A receives advertisements from three medical devices, charging device 20A may prioritize the three medical devices to determine an order in which charging device 20A wirelessly charges the three medical devices. Charging device 20A may, upon prioritizing the three medical devices, physically navigate within wireless charging range of the first medical device to wirelessly charge the first medical device. After wirelessly charging the first medical device, charging device 20A may physically navigate within wireless charging range of the second medical device to wirelessly charge the second medical device. After wirelessly charging the second medical device, charging device 20A may physically navigate within wireless charging range of the third medical device to wirelessly charge the third medical device.

Charging device 20A may be configured to determine a prioritization of a plurality of medical devices in any suitable manner based on any suitable combination of factors. In some examples, a lifesaving medical device, such as a pacemaker, may be prioritized over a non-lifesaving medical device, such as a monitoring medical device or a neurostimulation medical device. In some examples, each advertisement broadcasted by a medical device may indicate a deadline for the medical device to be wirelessly charged, and charging device 20A may prioritize a plurality of medical devices based on the deadline for each of the medical devices to be wirelessly charged, where a medical device having an earlier deadline to be wirelessly charged may be higher in the prioritization of the medical devices than a medical device having a later deadline to be wirelessly charged.

In some examples, charging device 20A may be configured to delegate wireless charging of a medical device if charging device 20A is unable to meet the medical device's deadline to be wirelessly charged. For example, if charging device 20A receives advertisements from a first medical device and a second medical device, charging device 20A may determine to prioritize wireless charging of the first medical device over the second medical device because the patient that is wearing the first medical device is about to go into surgery. However, charging device 20A may determine that it is unable to meet the second medical device's deadline to be wirelessly charged if charging device 20A has to wirelessly charge the first medical device prior to charging the second medical device.

Charging device 20A may therefore delegate the wireless charging of the second medical device to another charging device, such as to charging device 20B. To delegate the wireless charging of a medical device, such as medical device 16, to charging device 20B, charging device 20A may send the advertisement broadcasted by medical device 16 and received by charging device 20A to charging device 20B, such as via network 25. Charging device 20B may receive, from charging device 20A and via network 25, the advertisement broadcasted by medical device 16, and may treat the advertisement as if charging device 20B received the advertisement directly from medical device 16. Charging device 20B may therefore determine the physical location of medical device 16, move within wireless charging range of medical device 16, establish secure communications with medical devices to determine one or more parameters of the wireless charging between charging device 20B and medical device 16, and transmit power to medical device 16 to wirelessly charge medical device 16.

Figure 2:
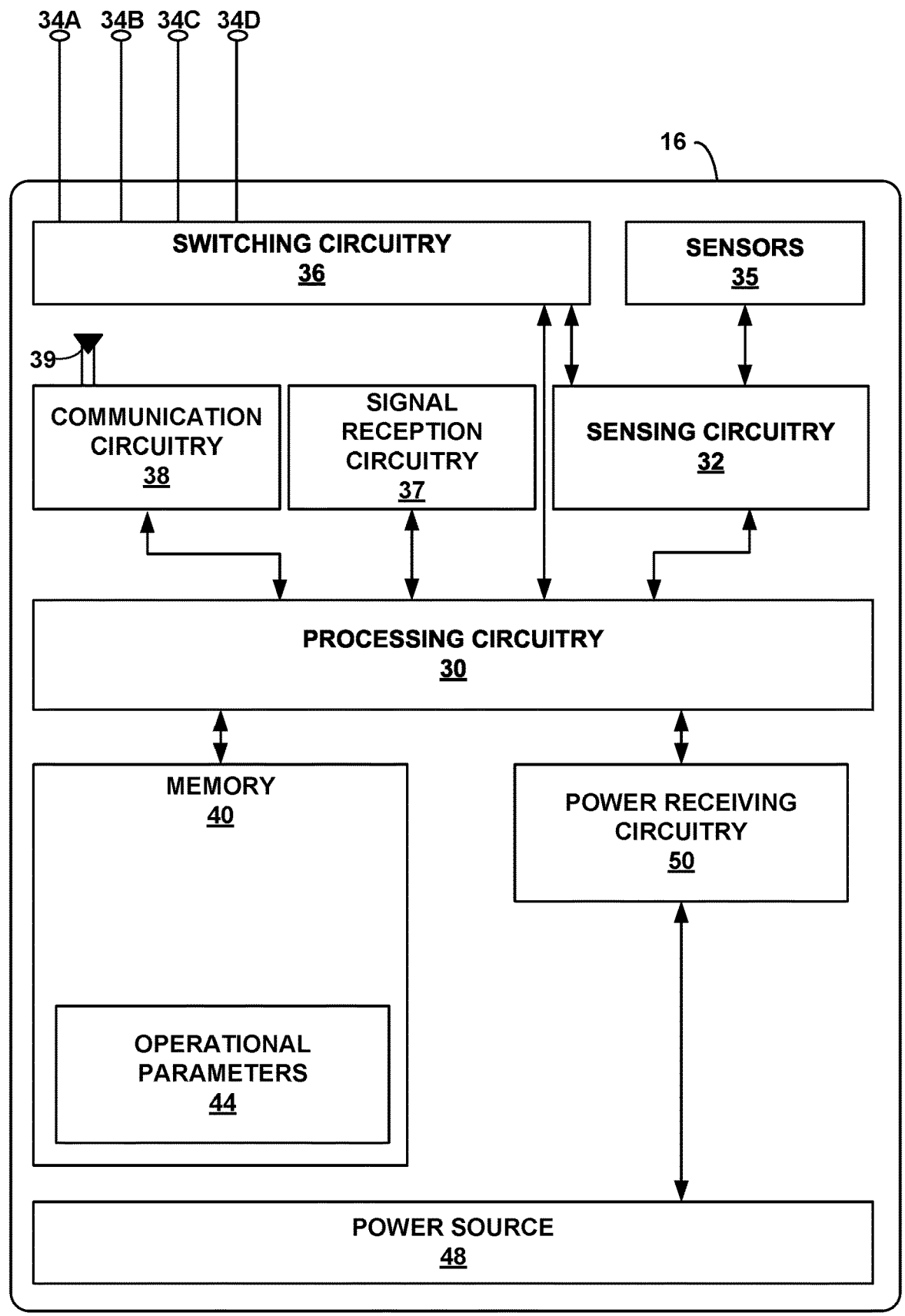
FIG. 2 is a block diagram illustrating an example configuration of components of an example medical device, in accordance with one or more techniques of this disclosure.

FIG. 2 is a block diagram illustrating an example configuration of components of medical device 16 in accordance with one or more techniques of this disclosure. In the example of FIG. 2, medical device 16 includes processing circuitry 30, sensing circuitry 32, electrodes 34A-34D (collectively, "electrodes 34"), sensors 35, switching circuitry 36, signal reception circuitry 37, communication circuitry 38, antenna 39, memory 40, power source 48, and power receiving circuitry 50. Memory 40 is configured to store operational parameters 44.

Processing circuitry 30, in one example, may include one or more processors that are configured to implement functionality and/or process instructions for execution within medical device 16. For example, processing circuitry 30 may be capable of processing instructions stored in memory 40. Processing circuitry 30 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 30 may include any suitable structure, whether in hardware, software, firmware, or any combination thereof, to perform the functions ascribed herein to processing circuitry 30.

Sensing circuitry 32 monitors electrical cardiac signals from any combination of electrodes 34A-34D (collectively, "electrodes 34"). In some examples, sensing circuitry 32 may include one or more amplifiers, filters, and analog-to-digital converters. For example, sensing circuitry 32 may include one or more detection channels, each of which may include an amplifier. The detection channels may be used to sense cardiac signals, such as a cardiac EGM. Some detection channels may detect events, such as R-waves, P-waves, and T-waves and provide indications of the occurrences of such events to processing circuitry 30. Additionally, or alternatively, some channels may detect cardiac EGM signals from a particular combination of electrodes 34. One or more other detection channels may provide signals to an analog-to-digital converter, for conversion into a digital signal for processing, analysis, storage, or output by processing circuitry 30.

Each detection channel of sensing circuitry 32 may include a filter configured to pass a custom range of frequency values. For example, sensing circuitry 32 may include one or more narrow band channels, each of which may include a narrow band filtered sense-amplifier. Additionally, or alternatively, sensing circuitry 32 may include one or more wide band channels, each of which include an amplifier with a relatively wider pass band than the narrow band channels. Signals sensed by the narrow band channels and the wide band channels of sensing circuitry 32 may be converted to multi-bit digital signals by an analog-to-digital converter (ADC) provided by, for example, sensing circuitry 32 or processing circuitry 30. In some examples, processing circuitry 30 analyzes the digitized version of signals from sensing circuitry 32. In other examples, processing circuitry 30 stores the digitized versions of the signals in memory 40 (e.g., as collected physiological data 45), outputs the digitized versions of the signals via communication circuitry 38, or any combination thereof.

Processing circuitry 30 may use switching circuitry 36 to select, e.g., via a data/address bus, which of electrodes 34 to use for sensing cardiac signals. Switching circuitry 36 may include a switch array, switch matrix, multiplexer, or any other type of switching device suitable to selectively couple energy to selected electrodes.

In some examples, sensing circuitry 32 is electrically coupled to sensors 35. Sensors 35 may include any combination of accelerometers, temperature sensors, chemical sensors, light sensors, and pressure sensors. Sensors 35 may, for example, sense one or more physiological parameters indicative of a heart condition. Additionally, or alternatively, an accelerometer of sensors 35 may sense data indicative of at least one of patient posture and patient activity.

Signal reception circuitry 37 may include hardware, firmware, software or any combination thereof for receiving signals from another device, such as external device 18. Signal reception circuitry 37 may be powered by power source 48, "listening" for signals from external device 18. In other examples, power source 48 may power signal reception circuitry 37 every 250 milliseconds (ms) for a period of time, where the period of time lasts for greater than 0.1 ms and less than 50 ms. In this way, signal reception circuitry 37 may alternate between an "off" state and an "on" state, where signal reception circuitry 37 is configured to detect signals while signal reception circuitry 37 is being powered by power source 48 during the on state.

Communication circuitry 38 may include any suitable hardware, firmware, software or any combination thereof for communicating with another device, such as external device 18. Under the control of processing circuitry 30, communication circuitry 38 may receive downlink telemetry from, as well as send uplink telemetry to, external device 18, one or more of charging devices 20, network 25, or another device with the aid of an internal or external antenna, e.g., antenna 39. In addition, processing circuitry 30 may communicate with a networked computing device via an external device (e.g., external device 18) and a computer network 25, such as the Medtronic CareLink® Network developed by Medtronic, plc, of Dublin, Ireland. Communication circuitry 38 may include any combination of a Bluetooth® radio, an electronic oscillator, frequency modulation circuitry, frequency demodulation circuitry, amplifier circuitry, and power switches such as a metal-oxide-semiconductor field-effect transistors (MOSFET), a bipolar junction transistor (BJT), an insulated-gate bipolar transistor (IGBT), a junction field effect transistor (JFET), or another element that uses voltage for its control. Signal reception circuitry 37 may, in some cases, be separate from communication circuitry 38. In other cases, signal reception circuitry 37 may be a component of, or a part of communication circuitry 38.

Memory 40 may be configured to store information within medical device 16 during operation. Memory 40 may include a computer-readable storage medium or computer-readable storage device. In some examples, memory 40 includes one or more of a short-term memory or a long-term memory. Memory 40 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, memory 40 is used to store data indicative of instructions for execution by processing circuitry 30.

In some examples, memory 40 is configured to store operational parameters 44. Operational parameters 44 may govern aspects of the operation of medical device 16. For example, operational parameters 44 may include combinations of electrodes 34 and sensors 35 for sensing physiological signals of patient 4. Additionally, or alternatively, operational parameters 44 may include a sampling rate for sampling analog signals sensed by electrodes 34 and sensors 35. Operational parameters 44 may be updated based on instructions received from an external device (e.g., external device 18) via communication circuitry 38. In some examples, processing circuitry 30 of medical device 16 updates operational parameters 44 only if instructions to update operational parameters 44 are received over a secure link.

Processing circuitry 30 is configured to determine and track power source statistics associated with power source 48, such as the remaining battery life and/or capacity of power source 48, the discharge rate of power source 48, a predicted future discharge rate of power source 48, and/or any other suitable information, and may determine, based on the power source statistics, whether to broadcast advertisements to request wireless charging of power source 48 by one or more of charging devices 20. For example, processing circuitry 30 may compare the remaining battery life and/or capacity of power source 48 to one or more thresholds. If processing circuitry 30 determines that the remaining battery life and/or capacity of power source 48 is less than the one or more thresholds, processing circuitry 30 may broadcast, via communication circuitry 38 and to, for example, network 25, advertisements that are requests for wireless charging by a charging device.

In some examples, the advertisement broadcasted by processing circuitry 30 may indicate a deadline for medical device 16 to be wirelessly charged. Such a deadline may indicate, for example, a time by which medical device 16 is to be wirelessly charged. Processing circuitry 30 may determine the deadline for medical device 16 to be wirelessly charged based on any suitable combination of factors. For example, if processing circuitry 30 determines, based on the discharge rate of power source 48 that the battery life of power source 48 will drop below a battery life threshold, such as 10% battery life, 20% battery life, and the like, by a certain time, such as in 20 minutes, the advertisement may indicate a deadline of 20 minutes for medical device 16 to be wirelessly charged. In another example, processing circuitry 30 may determine the deadline for medical device 16 to be wirelessly charged based on a status of patient 4. For example, if patient 4 is scheduled to be in surgery in 30 minutes, processing circuitry 30 may determine that medical device 16 should be wirelessly charged 10 minutes before patient 4 undergoes surgery, and processing circuitry 30 may broadcast an advertisement that indicates a deadline of 20 minutes for medical device 16 to be wirelessly charged.

In some examples, processing circuitry 30 is configured to determine location information associated with medical device 16 and to send the determined location information via network 25 to one or more of charging devices 20. In some examples, if medical device 16 includes a location sensor, such as a GPS sensor, processing circuitry 30 may determine location information associated with medical device 16 using the location sensor and may send the location information associated with medical device 16 to network 25.

In some examples, communication circuitry 38 may communicate with one or more beacons, such as Bluetooth Low Energy beacons, to determine the location of medical devices 16 within a facility. For example, communication circuitry 38 may receive location information from one or more beacons indicative of the location of the location of medical device 16 within a facility, such as the room number where medical device 16 is located, the wing of the facility where medical device 16 is located. Processing circuitry 30 may therefore send such location information associated with medical device 16 to network 25.

In response to broadcasting the advertisements, medical device 16 may receive, via communication circuitry 38 and from charging device 20A, a request to establish secure communications with medical device 16. Processing circuitry 30 may therefore communicate with charging device 20A via communication circuitry 38 to establish secure communications with charging device 20A.

In some examples, as part of establishing secure communications with charging device 20A, processing circuitry 30 may verify the identity of charging device 20A to determine that charging device 20A is authorized to perform wireless charging of medical device 16 via any suitable authentication technique. For example, medical device 16 may receive a password from charging device 20A, and processing circuitry 30 may determine whether the password from charging device 20A is a password associated with a charging device that is authorized to perform wireless charging of medical device 16. If processing circuitry 30 determines that the password from charging device 20A is a password associated with a charging device that is authorized to perform wireless charging of medical device 16, processing circuitry 30 may authenticate charging device 20A as charging device that is authorized to perform wireless charging of medical device 16. In some examples, power receiving circuitry 50 of medical device 16 may be powered off by default. Processing circuitry 30 may, in response to successfully authenticating charging device 20A as charging device that is authorized to perform wireless charging of medical device 16, turn on power receiving circuitry 50 to receive power that is wirelessly transmitted from charging device 20A.

In some examples, to establish secure communications between medical device 16 and charging device 20A, medical device 16 and charging device 20A may encrypt data sent between medical device 16 and charging device 20A. In some examples, charging device 20A may send an encryption key to medical device 16 for medical device 16 to encrypt data sent to charging device 20A, and medical device 16 may correspondingly send an encryption key to charging device 20A to encrypt data sent to medical device 16. In some examples, charging device 20A may encrypt data to be sent to medical device 16 using a public encryption key associated with medical device 16, and medical device 16 may encrypt data to be sent to charging device 20A using a public encryption key associated with charging device 20A.

Medical device 16 may, in response to establishing secure communications with charging device 20A, send, to charging device 20A, one or more parameters associated with wirelessly charging medical device 16. The one or more parameters may include the amount of power (e.g., number of Watts) to be wirelessly transmitted by charging device 20A, the duration of the wireless power transmission by charging device 20A, and the like.

In some examples, medical device 16 may, in response to establishing secure communications with charging device 20A, broadcast an indication that medical device 16 is about to start being wirelessly charged by charging device 20A. Broadcasting such an indication that medical device 16 is about to start being wirelessly charged by charging device 20A may enable medical devices within the physical vicinity of medical device 16 to turn off their power receiving circuitry to avoid being damaged by the power to be wirelessly transmitted by charging device 20A. Similarly, when medical device 16 receives a broadcast from another medical device indicating that the other medical device is about to start being wirelessly charged, processing circuitry 30 may, in response, turn off power receiving circuitry 50.

Power receiving circuitry 50 may include hardware components and circuitry configured to wirelessly receive power (e.g., electrical energy) transmitted by one or more of charging devices 20 and to re-charge power source 48 with the energy of the power received by power receiving circuitry 50. Examples of power receiving circuitry 50 may include one or more rectennas, photovoltaic laser power converters, and the like. Once medical device 16 has communicated one or more parameters associated with wirelessly charging medical device 16 to charging device 20A, power receiving circuitry 50 may start to wirelessly receive power being transmitted by charging device 20A. Power receiving circuitry 50 may therefore use the power received from charging device 20A to re-charge power source 48.

Power source 48 is configured to deliver operating power to the components of medical device 16. Power source 48 may include a battery and a power generation circuit to produce the operating power. In some examples, the battery is rechargeable to allow extended operation. In some examples, recharging is accomplished through proximal inductive interaction between an external charger and an inductive charging coil within external device 18. Power source 48 may include any one or more of a plurality of different battery types, such as nickel cadmium batteries and lithium ion batteries.

Figure 3:
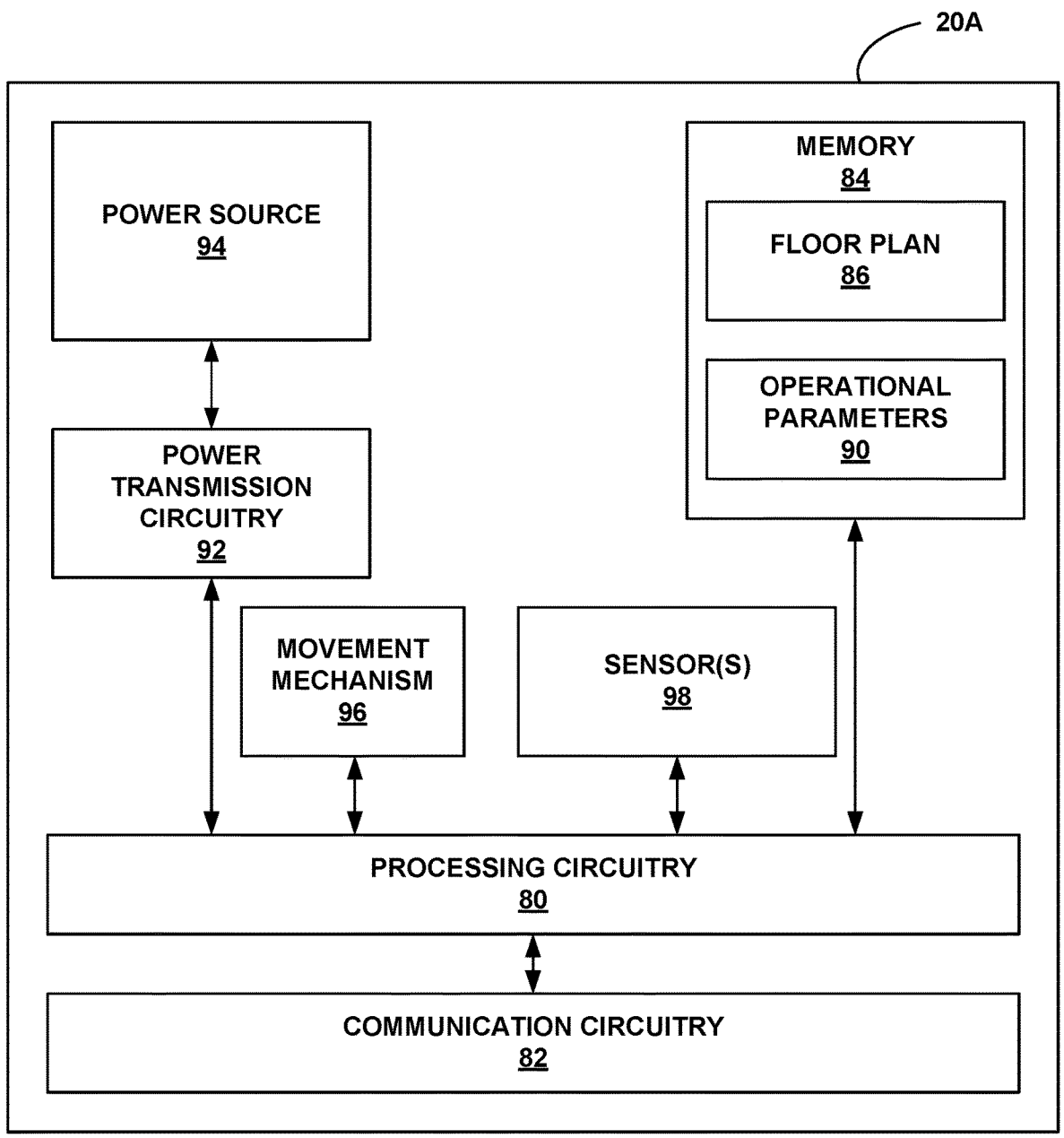
FIG. 3 is a block diagram illustrating an example configuration of components of an example charging device, in accordance with one or more techniques of this disclosure.

FIG. 3 is a block diagram illustrating an example configuration of components of charging device 20A in accordance with one or more techniques of this disclosure. In the example of FIG. 3, charging device 20A includes processing circuitry 80, communication circuitry 82, memory 84, power transmission circuitry 92, one or more sensors 98, and power source 94.

Processing circuitry 80, in one example, may include one or more processors that are configured to implement functionality and/or process instructions for execution within charging device 20A. For example, processing circuitry 80 may be capable of processing instructions stored in memory 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

One or more sensors 98, in one example, may include any suitable sensor components that may be used to assist charging device 20A to navigate to medical device 16 to wirelessly charge medical device 16 and/or to assist charging device 20A to identify medical device 16 for the purposes of wirelessly charging medical device 16. One or more sensors 98 may include one or more image sensors (e.g., one or more cameras), one or more laser imaging, detection, and ranging (LIDAR) sensors, and the like. For example, processing circuitry 80 may be configured to use one or more sensors 98 to detect obstacles in the path of charging device 20A, so that processing circuitry 80 may be able to navigate around such obstacles to reach medical device 16.

In some examples, processing circuitry 80 may be configured to use one or more sensors 98 to determine whether a medical device is medical device 16 that is to be wirelessly charged by charging device 20A. For example, image sensors of one or more sensors 98 may capture images of a QR code on or displayed by medical device 16 that contains identification information associated with medical device 16, so that processing circuitry 80 may use the QR code to determine the identity of the associated medical device. In some examples, image sensors of one or more sensors 98 may capture images of a medical device, and processing circuitry 80 may be configured to perform image recognition of the captured images to recognize a medical device as medical device 16.

For example, when processing circuitry 80 determines that charging device 20A is within wireless charging range of medical device 16, processing circuitry 80 may be able to identify medical device 16 using one or more sensors 98, such as via image recognition, scanning QR codes, and the like. Processing circuitry 80 may, based on identifying medical device 16, be able to position power transmission circuitry 92 to optimize the wireless charging to medical device 16. For example, if power transmission circuitry 92 is a directional power charging circuitry, processing circuitry 80 may use one or more sensors 98, such as via image recognition, scanning QR codes, and the like, to determine the direction of medical device 16 with respect to charging device 20A. Processing circuitry 80 may be configured to, based on the determined direction of medical device 16 with respect to charging device 20A, move charging device 20A (e.g., via movement mechanism 96) and/or move power transmission circuitry 92 in order to orient power transmission circuitry 92 towards the direction of medical device 16 to perform wireless charging of medical device 16.

In some examples, charging device 20A is a robotic device that includes components and/or mechanisms, such as movement mechanism 96, such as motorized wheels, robotic legs, and the like configured to move charging device 20A across different locations in a facility. Movement mechanism 96 may, in some examples, contain a motor or other electro-mechanical components for driving the wheels and/or robotic legs. Processing circuitry 80 may be configured to control movement mechanism 96 to use control movement mechanism 96 to physically move charging device 20A. For example, processing circuitry 80 may be configured to send drive signals to movement mechanism 96 that causes movement mechanism 96 to operate to move charging device 20A. If movement mechanism 96 includes multiple movement components, such as multiple wheels or multiple robotic legs, processing circuitry 80 may be configured to send drive signals to movement mechanism 96 to control individual components, such as an individual wheel and/or an individual robotic leg, in order to finely control the movements of such movement components and to make fine-grained adjustments regarding the movement of charging device 20A.

Communication circuitry 82 may include any suitable hardware, firmware, software or any combination thereof for communicating with another device, such as IMD. Under the control of processing circuitry 80, communication circuitry 82 may receive downlink telemetry from, as well as send uplink telemetry to, medical device 16, external device 18, one or more other charging devices 20, charging system 10, and or other computing devices via a network, such as via network 25.

In some examples, communication circuitry 82 includes any combination of a Bluetooth radio, an electronic oscillator, frequency modulation circuitry, frequency demodulation circuitry, amplifier circuitry, and power switches such as a MOSFET, a BJT, an IGBT, a JFET, or another element that uses voltage for its control.

Memory 84 may be configured to store information within charging device 20A during operation. Memory 84 may include a computer-readable storage medium or computer-readable storage device. In some examples, memory 84 includes one or more of a short-term memory or a long-term memory. Memory 84 may include, for example, RAM, DRAM, SRAM, magnetic discs, optical discs, flash memories, or forms of EPROM or EEPROM. In some examples, memory 84 is used to store data indicative of instructions for execution by processing circuitry 80. Memory 84 may be used by software or applications running on charging device 20A to temporarily store information during program execution.

Power source 94 is configured to deliver operating power to the components of charging device 20A. Power source 94 may include a battery and a power generation circuit to produce the operating power. In some examples, the battery is rechargeable to allow extended operation. Recharging may be accomplished by electrically coupling power source 94 to a cradle or plug that is connected to an alternating current (AC) outlet. In addition, recharging may be accomplished through proximal inductive interaction between an external charger and an inductive charging coil within charging device 20A. In other examples, traditional batteries (e.g., nickel cadmium or lithium ion batteries) may be used. In addition, charging device 20A may be directly coupled to an alternating current outlet to operate.

Power transmission circuitry 92 is configured to receive power from power source 94 and to wirelessly transmit power to one or more medical devices, such as medical device 16. Power transmission circuitry 92 may wirelessly transmit power (e.g., electrical energy) using any suitable wireless power transmission technique, such as by transmitting ultrasonic energy, magnetic induction, transmitting radio waves (e.g., in the microwave range), transmitting laser beams, and the like. Power transmission circuitry 92 may be able to wirelessly transmit power from 1 Watt up to 20 Watts or more to a medical device within wireless charging distance of charging device 20A, such as within two meters of charging device 20A. In some examples, power transmission circuitry 92 may be configured to simultaneously perform wireless charging of two or more medical devices within wireless charging range of charging device 20A by wirelessly transmitting power to each of the two or more medical devices.

Charging device 20A may receive a request to perform wireless charging of a medical device, such as medical device 16. The request may indicate the medical device, such as medical device 16, that charging device 20A is requested to wirelessly charge. In some examples, charging device 20A may receive the request in the form of one or more advertisements broadcasted by medical device 16 and/or external device 18 and received by charging device 20A over network 25. In some examples, charging device 20A may receive the request from charging system 10. In some examples, charging device 20A may receive the request in the form of a delegation request from another one of charging devices 20 to delegate wireless charging of medical device 16 to charging device 20A.

In some examples, charging device 20A may receive user input at a user input device (not shown) of charging device 20A that is indicative of a request to perform wireless charging of medical device 16. Examples of such user input may include user input at a touchscreen of charging device 20A, a voice command received at an audio input component of charging device 20A, an audible alert generated by medical device 16 and/or external device 18 and received at an audio input component of charging device 20A, and the like.

In some examples, the request to perform wireless charging may indicate a location of medical device 16 to be wirelessly charged and/or a deadline for wirelessly charging medical device 16. Charging device 20A may determine, based on the location of medical device 16 and/or the deadline for wirelessly charging medical device 16, whether charging device 20A is to wirelessly charge medical device 16 or whether to delegate wireless charging of medical device 16 to another one of charging devices 20.

In some examples, processing circuitry 80 of charging device 20A may be configured to receive requests to charge two or more medical devices and may determine a prioritization of the two or more medical devices to wirelessly charge. Charging device 20A may therefore wirelessly charge higher priority medical devices in the prioritization of medical devices before proceeding to wirelessly charge lower priority medical devices.

In some examples, charging device 20A may wirelessly charge a higher priority medical device at the same time as a lower priority medical device if both the higher priority medical device and the lower priority medical device are both within wireless charging of charging device 20A. For example, when processing circuitry 80 determines to wirelessly charge the medical device having the highest priority in the prioritization, processing circuitry 80 may determine that not only is the medical device having the highest priority in the prioritization is within wireless charging distance of charging device 20A, but that a medical device having a lower priority in the prioritization is also within wireless charging distance of charging device 20A. Processing circuitry 80 may therefore determine to wirelessly charge both the medical device having the highest priority in the prioritization and the medical device having a lower priority in the prioritization when both medical devices are within wireless charging distance of charging device 20A.

Processing circuitry 80 may be configured to determine a prioritization of two or more medical devices to wirelessly charge in any suitable manner. In some examples, processing circuitry 80 may prioritize a medical device associated with a nearer deadline for wirelessly charging the medical device over a medical device associated with a later deadline for wirelessly charging the medical device. In some examples, processing circuitry 80 may prioritize a medical device physically located closer to charging device 20A over a medical device physically located farther away from charging device 20A. In other examples, processing circuitry 80 may use any suitable combination of the deadlines associated with the medical devices, the locations of the medical devices, and any other suitable factors to determine the prioritization of two or more medical devices.

Processing circuitry 80 may therefore determine, based on the prioritization of a medical device 16, whether charging device 20A will be able to meet the deadline for wirelessly charging the medical device 16. If processing circuitry 80 determines that charging device 20A will not be able to meet the deadline for wirelessly charging the medical device 16, charging device 20A may communicate with one or more other charging devices 20, such as via network 25, to delegate the wireless charging of the medical device 16 to another one of charging devices 20.

Processing circuitry 80 may, in response to determining to charge medical device 16, determine the location of medical device 16 and may navigate charging device 20A to physically move within wireless charging range of medical device 16. Processing circuitry 80 may use a floor plan 86 of a facility where charging device 20A and medical device 16 are located stored in memory 84 and the location of medical device 16 to navigate the facility, so that charging device 20A may use movement mechanism 96 to physically move within wireless charging range of medical device 16. In some examples, processing circuitry 80 may have previously received floor plan 86 via network 25 from computing system 24 and/or charging system 10.

In some examples, charging device 20A may include one or more image sensors (e.g., one or more cameras), one or more laser imaging, detection, and ranging (LIDAR) sensors, and the like that may assist charging device 20A in navigating a facility based on floor plans 86 of the facility to reach medical device 16. For example, charging device 20A may use such image sensors and/or LIDAR sensors to sense and navigate around obstacles in order to physically move through the facility towards wireless charging range of medical device 16.

Processing circuitry 80 may, in response to determining to charge medical device 16, also establish, via communication circuitry 82, a secure communication session with medical device 16 to authenticate charging device 20A with medical device 16 and to negotiate one or more parameters of wireless charging of medical device 16. For example, charging device 20A may send a password to medical device to indicate that charging device 20A is authorized to perform wireless charging of medical device 16.

In some examples, to establish secure communications between medical device 16 and charging device 20A, medical device 16 and charging device 20A may encrypt data sent between medical device 16 and charging device 20A. In some examples, charging device 20A may send an encryption key to medical device 16 for medical device 16 to encrypt data sent to charging device 20A, and charging device 20A may receive a corresponding encryption key from medical device 16 to encrypt data sent to medical device 16. In some examples, charging device 20A may encrypt data to be sent to medical device 16 using a public encryption key associated with medical device 16, and medical device 16 may encrypt data to be sent to charging device 20A using a public encryption key associated with charging device 20A.

Charging device 20A may, in response to establishing secure communications with medical device 16, receive, from medical device 16, one or more parameters associated with wirelessly charging medical device 16. The one or more parameters may include the amount of power (e.g., number of Watts) to be wirelessly transmitted by charging device 20A, the duration of the wireless power transmission by charging device 20A, and the like. Processing circuitry 80 may therefore configure power transmission circuitry 92 to wirelessly transmit power according to the one or more parameters and may enable power transmission circuitry 92 to wirelessly transmit power to medical device 16 according to the one or more parameters.

In some examples, charging device 20A may, prior to starting to wirelessly transmit power to medical device 16, broadcast an indication that medical device 16 is about to start being wirelessly charged by charging device 20A. Broadcasting such an indication that medical device 16 is about to start being wirelessly charged by charging device 20A may enable medical devices within the wireless charging range of charging device 20A to turn off their power receiving circuitry to avoid being damaged by the power to be wirelessly transmitted by charging device 20A. For example, charging device 20A may broadcast an indication of an identifier of medical device 16 as part of broadcasting the indication that medical device 16 is about to start being wirelessly charged by charging device 20A. A medical device that receives the broadcast form charging device 20A may determine whether the medical device's identifier matches the broadcasted identifier of medical device 16. If the medical device determines that the medical device's identifier does not match the broadcasted identifier of medical device 16, the medica device may turn off the medical device's power receiving circuitry.

As charging device 20A wirelessly transmits power to medical device 16, processing circuitry 80 of charging device 20A may monitor the location and/or movement of medical device 16, such as by using the techniques described throughout this disclosure. In some examples, processing circuitry 80 may adjust the wireless transmission of power by charging device 20A to medical device 16 based on the detected movement and/or changes in location by medical device 16. For example, when processing circuitry 80 determines that medical device 16 has moved and/or changed locations, charging device 20A may move, using movement mechanism 96, from its current location to a new location that corresponds to the new location of medical device 16 to continue to wirelessly transmit power to medical device 16. In some examples, if charging device 20A includes physical mechanisms for moving the position of power transmission circuitry 92, charging device 20A may use such physical mechanisms to move the position of power transmission circuitry 92 based on the movements of medical device 16 to direct power transmission circuitry 92 towards the direction and/or location of medical device 16 to continue to wirelessly transmit power to medical device 16. In some examples, when processing circuitry 80 determines that medical device 16 has moved and/or changed locations, processing circuitry 80 may also send, via communication circuitry 82 to a device associated with a caretaker or clinician of a patient that uses medical device 16, a notification indicative of the movement and/or changed locations of the patient.

Figure 4:
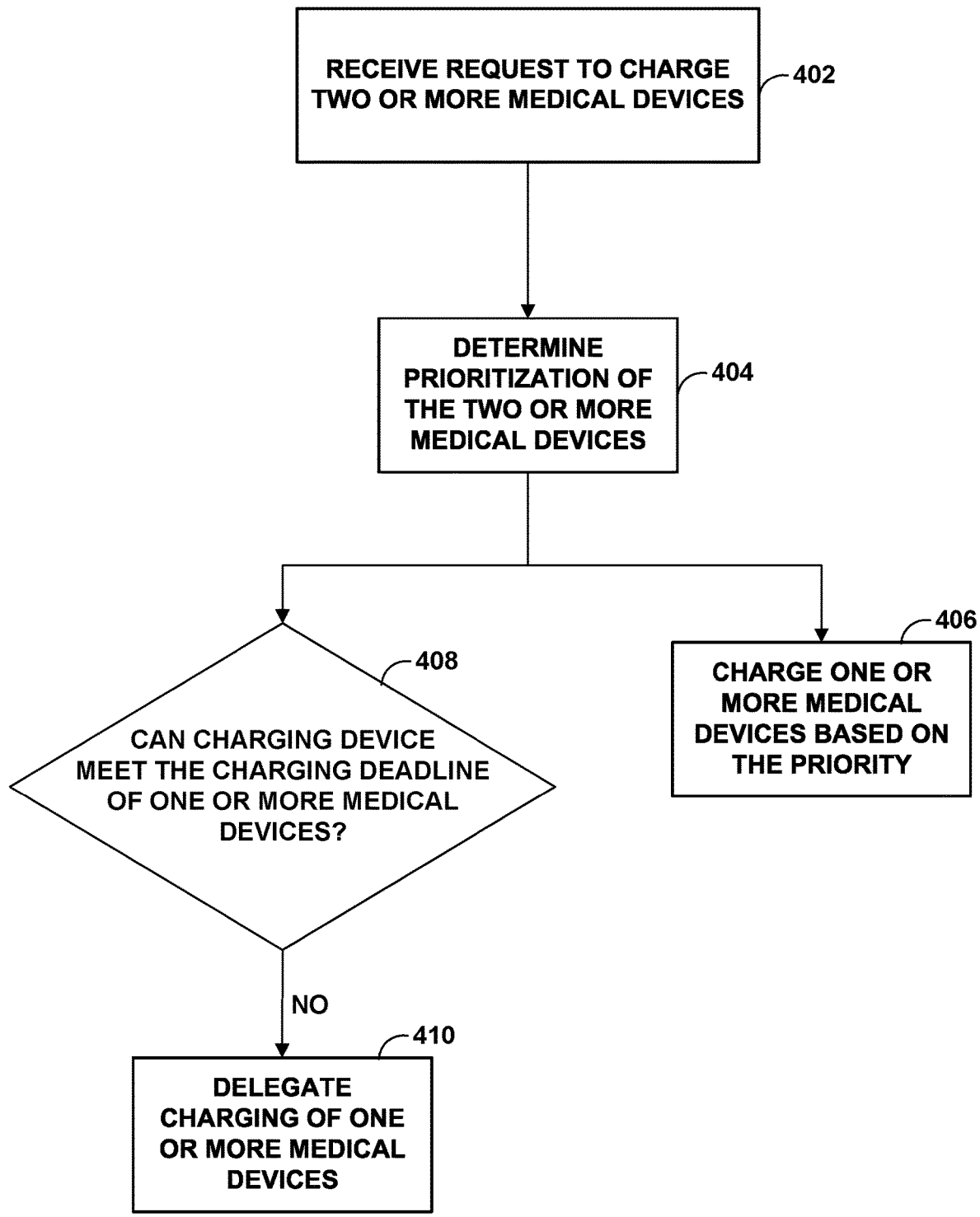
FIG. 4 is a flow diagram illustrating an example operation of an example charging device 20A, in accordance with one or more techniques of this disclosure.

FIG. 4 is a flow diagram illustrating an example operation of an example charging device 20A, in accordance with one or more techniques of this disclosure. The example operation is described with respect to charging device 20A and medical device 16 of FIGS. 1-3, and components thereof.

As shown in FIG. 4, charging device 20A may receive one or more requests to wirelessly charge two or more medical devices (402). For example, charging device 20A may receive, from each of two or more medical devices, a request to wirelessly charge a respective medical device. In some examples, charging device 20A may receive (e.g., from charging system 10 and/or computing system 24) one or more requests to wirelessly charge two or more medical devices.

The one or more requests may include information associated with each of the two or more medical devices that charging device 20A is requested to charge, such as the identity of each of the two or more medical devices, information regarding the type of each of the two or more medical devices, the location of each of the two or more medical devices, a deadline to be wirelessly charged of each of the two or more medical devices, and/or any other information that charging device 20A may use to determine a prioritization of the two or more medical devices.

Charging device may, in response to receiving the one or more requests to wirelessly charge the two or more medical devices, determine a prioritization of the two or more medical devices based at least in part on the information associated with each of the two or more medical devices (404). By determining a prioritization of the two or more medical devices, charging device 20A may determine an order in which to charge each of the two or more medical devices.

Charging device 20A may, upon prioritizing the two or more medical devices, wirelessly charge the medical device having the highest priority out of the two or more medical devices (406). For example, charging device 20A may physically navigate within wireless charging range of the medical device having the highest priority to wirelessly charge the medical device. After wirelessly charging the medical device having the highest priority, charging device 20A may physically navigate within wireless charging range of the medical device having the next highest priority to wirelessly charge that medical device.

In some examples, charging device 20A may delegate wireless charging of a medical device if charging device 20A is unable to meet the medical device's deadline to be wirelessly charged. For example, if the two or more medical devices include a first medical device and a second medical device, charging device 20A may determine to prioritize wireless charging of the first medical device over the second medical device. However, if charging device 20A determines that it is unable to meet the second medical device's deadline to be wirelessly charged if charging device 20A has to wirelessly charge the first medical device prior to charging the second medical device, charging device 20A may delegate the wireless charging of the second medical device to another charging device, such as to charging device 20B.

As such, charging device 20A may determine whether charging device 20A is unable to meet one or more medical devices' deadline to be wirelessly charged (408). Charging device 20A may, in response to determining that charging device 20A is unable to meet one or more medical devices' deadline to be wirelessly charged (NO of 408), delegate wireless charging of the one or more medical devices (410). In some examples, charging device 20A may, in response to determining that charging device 20A is able to meet one or more medical devices' deadline to be wirelessly charged (YES of 408), wirelessly charge a medical device out of the two or more medical devices based on the prioritization of the two or more medical devices (406).

Figure 5:
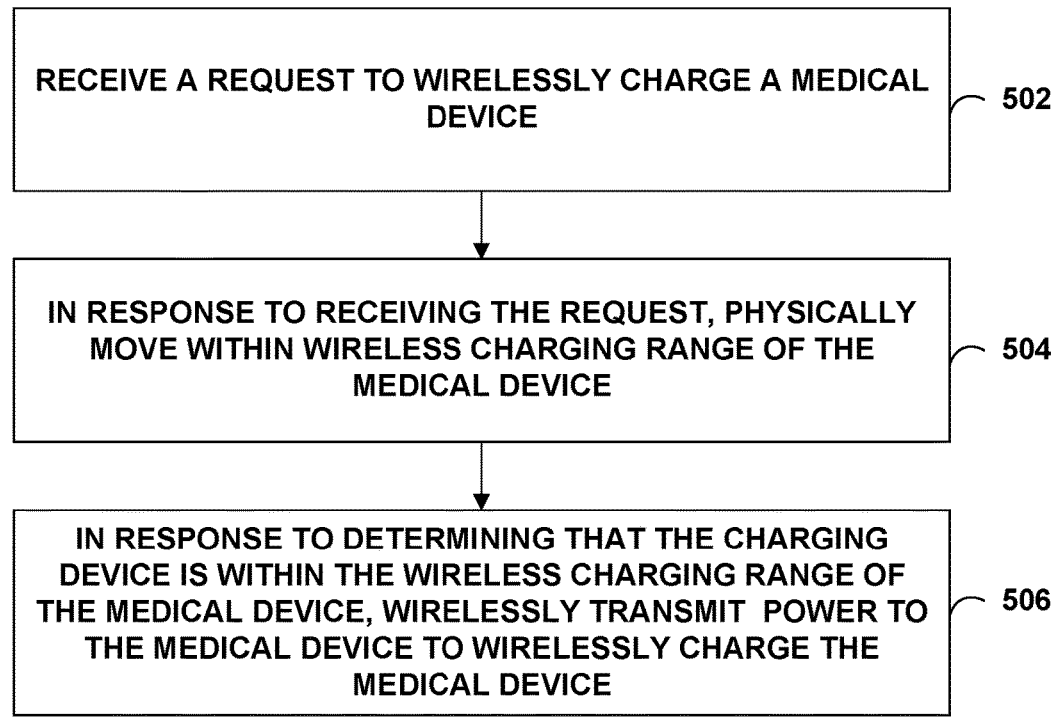
FIG. 5 is a flow diagram illustrating an example operation in accordance with one or more techniques of this disclosure.

FIG. 5 is a flow diagram illustrating an example operation in accordance with one or more techniques of this disclosure. The example operation is described with respect to charging device 20A and medical device 16 of FIGS. 1-3, and components thereof.

As shown in FIG. 5, processing circuitry 80 of charging device 20A may receive a request to wirelessly charge a medical device 16 (502). Charging device 20A may, in response to receiving the request, physically move within wireless charging range of the medical device 16 (504). Power transmission circuitry 92 of the charging device 20A may, in response to charging device 20A determining that the charging device 20A is within the wireless charging range of the medical device 16, wirelessly transmit power to the medical device 16 to wirelessly charge the medical device 16 (506).

In some examples, to physically move within wireless charging range of the medical device 16, processing circuitry 80 may determine a location of the medical device 16, and the charging device 20A may physically move to the location of the medical device 16. In some examples, the location of the medical device 16A comprises Global Positioning System (GPS) information. In some examples, the location of the medical device 16 comprises a room of a facility. In some examples, to physically move to the location of the medical device 16, the charging device 20A may navigate, using a floor plan of a facility, the facility to reach the location of the medical device 16.

In some examples, the processing circuitry 80 may establish a secure communication session with the medical device 16. The processing circuitry 80 may receive, from the medical device 16, one or more parameters associated with wirelessly charging the medical device 16. The processing circuitry 80 may configure the power transmission circuitry 92 of the charging device 20A to wirelessly transmit power to the medical device 16 according to the one or more parameters.

In some examples, to receive the request to wirelessly charge medical device 16, the processing circuitry may receive a plurality of requests to wirelessly charge a plurality of medical devices including the medical device 16. The processing circuitry 80 may determine a prioritization of the plurality of medical devices. The power transmission circuitry 92 may wirelessly charge one or more of the plurality of medical devices based at least in part on the prioritization of the plurality of medical devices.

In some examples, to determine the prioritization of the plurality of the medical devices, the processing circuitry 80 may determine deadlines to be wirelessly charged associated with the plurality of medical devices, and may determine the prioritization of the plurality of medical devices based at least in part on the deadlines to be wirelessly charged associated with the plurality of medical devices.

In some examples, the processing circuitry 80 may determine that the charging device 20A is unable to meet one or more of the deadlines to be wirelessly charged associated with a second one or more of the plurality of medical devices and may, in response to determining that the charging device 20A is unable to meet the one or more of the deadlines to be wirelessly charged associated with the second one or more of the plurality of medical devices, delegate wireless charging of the second one or more of the plurality of medical devices to one or more other charging devices.

In some examples, the processing circuitry 80 may, prior to wirelessly transmitting power to the medical device 16, broadcast an indication the charging device 20A is about to wirelessly transmit power to the medical device 16 to enable one or more other medical devices within wireless charging range of the charging device 20A to turn off respective power receiving circuitry of each of the one or more other medical devices.

Aspects of this disclosure includes the following examples.

Example 1. A method comprising: receiving, by processing circuitry of a charging device, a request to wirelessly charge a medical device; in response to receiving the request, physically moving, by the charging device, within wireless charging range of the medical device; and when the charging device is within the wireless charging range of the medical device, wirelessly transmitting, by power transmission circuitry of the charging device, power to the medical device to wirelessly charge the medical device.

Example 2. The method of example 1, wherein receiving the request to wirelessly charge the medical device further comprises: receiving, by the processing circuitry of the charging device, one or more advertisements broadcasted by the medical device.

Example 3. The method of example 1, wherein receiving the request to wirelessly charge the medical device further comprises: receiving, by the processing circuitry, a delegation request from another charging device to wirelessly charge the medical device.

Example 4. The method of example 1, wherein receiving the request to wirelessly charge the medical device further comprises: receiving, by the processing circuitry, user input indicative of the request to wirelessly charge the medical device.

Example 5. The method of example 4, wherein the user input comprises a voice command to wirelessly charge the medical device.

Example 6. The method of any of examples 1-5, wherein physically moving within wireless charging range of the medical device further comprises: determining, by the processing circuitry, a location of the medical device; and physically moving, by the charging device, to the location of the medical device.

Example 7. The method of example 6, wherein the location of the medical device comprises Global Positioning System (GPS) information.

Example 8. The method of example 6, wherein the location of the medical device comprises a room of a facility.

Example 9. The method of any of examples 6-8, wherein physically moving to the location of the medical device further comprises: navigating, by the charging device using a floor plan of a facility, the facility to reach the location of the medical device.

Example 10. The method of any of examples 1-9, further comprising: establishing, by the processing circuitry, a secure communication session with the medical device; receiving, by the processing circuitry from the medical device, one or more parameters associated with wirelessly charging the medical device; and configuring, by the processing circuitry, the power transmission circuitry of the charging device to wirelessly transmit power to the medical device according to the one or more parameters.

Example 11. The method of any of examples 1-10, wherein receiving the request to wirelessly charge medical device further comprises receiving, by the processing circuitry, a plurality of requests to wirelessly charge a plurality of medical devices including the medical device, further comprising: determining, by the processing circuitry, a prioritization of the plurality of medical devices; and wirelessly charging, by the power transmission circuitry, one or more of the plurality of medical devices based at least in part on the prioritization of the plurality of medical devices.

Example 12. The method of example 11, wherein determining the prioritization of the plurality of the medical devices further comprises: determining, by the processing circuitry, deadlines to be wirelessly charged associated with the plurality of medical devices; and determining, by the processing circuitry, the prioritization of the plurality of medical devices based at least in part on the deadlines to be wirelessly charged associated with the plurality of medical devices.

Example 13. The method of example 12, further comprising: determining, by the processing circuitry, that the charging device is unable to meet one or more of the deadlines to be wirelessly charged associated with a second one or more of the plurality of medical devices; and in response to determining that the charging device is unable to meet the one or more of the deadlines to be wirelessly charged associated with the second one or more of the plurality of medical devices, delegating, by the processing circuitry, wireless charging of the second one or more of the plurality of medical devices to one or more other charging devices.

Example 14. The method of any of examples 1-13, further comprising: prior to wirelessly transmitting power to the medical device, broadcasting, by the processing circuitry, an indication the charging device is about to wirelessly transmit power to the medical device to enable one or more other medical devices within wireless charging range of the charging device to turn off respective power receiving circuitry of each of the one or more other medical devices.

Example 15. A charging device configured to wirelessly transmit power, wherein the charging device comprises: movement mechanism configured to physically move the charging device; communication circuitry configured for wireless communication; power transmission circuitry configured to wirelessly transmit power; and processing circuitry electrically coupled to the movement mechanism, the communication circuitry, and the power transmission circuitry, wherein the processing circuitry is configured to: receive, via the communication circuitry, a request to wirelessly charge a medical device; and in response to receiving the request, cause the movement mechanism to physically move the charging device within wireless charging range of the medical device; wherein the power transmission circuitry is further configured to, when the charging device is within the wireless charging range of the medical device, wirelessly transmit power to the medical device to wirelessly charge the medical device.

Example 16. The charging device of example 15, wherein to receive the request to wirelessly charge the medical device, the processing circuitry is further configured to: receive, via the communication circuitry, one or more advertisements broadcasted by the medical device.

Example 17. The charging device of example 15, wherein to receive the request to wirelessly charge the medical device, the processing circuitry is further configured to: receive, via the communication circuitry, a delegation request from another charging device to wirelessly charge the medical device.

Example 18. The charging device of example 15, wherein to receive the request to wirelessly charge the medical device, the processing circuitry is further configured to: receive, via the communication circuitry, user input indicative of the request to wirelessly charge the medical device.

Example 19. The charging device of example 18, wherein the user input comprises a voice command to wirelessly charge the medical device.

Example 20. The charging device of any of examples 15-19, wherein: the processing circuitry is further configured to determine a location of the medical device; and to physically move the charging device within wireless charging range of the medical device, the movement mechanism is further configured to physically move the charging device to the location of the medical device.

Example 21. The charging device of example 20, wherein the location of the medical device comprises Global Positioning System (GPS) information.

Example 22. The charging device of example 20, wherein the location of the medical device comprises a room of a facility.

Example 23. The charging device of any of examples 20-22, wherein processing circuitry is further configured to: navigate a facility using a floor plan of the facility, the facility to cause the movement mechanism to physically move the charging device to reach the location of the medical device.

Example 24. The charging device of any of examples 15-23, wherein the processing circuitry is further configured to: establish, via the communication circuitry, a secure communication session with the medical device; receive, via the communication circuitry and from the medical device, one or more parameters associated with wirelessly charging the medical device; and configure the power transmission circuitry of the charging device to wirelessly transmit power to the medical device according to the one or more parameters.

Example 25. The charging device of any of examples 15-24, wherein to receive the request to wirelessly charge the medical device, the processing circuitry is further configured to: receive, via communication circuitry, a plurality of requests to wirelessly charge a plurality of medical devices including the medical device, further comprising: determine a prioritization of the plurality of medical devices; and cause the power transmission circuitry to wirelessly charge one or more of the plurality of medical devices based at least in part on the prioritization of the plurality of medical devices.

Example 26. The charging device of example 25, wherein to determine the prioritization of the plurality of medical devices, the processing circuitry is further configured to: determine deadlines to be wirelessly charged associated with the plurality of medical devices; and determine the prioritization of the plurality of medical devices based at least in part on the deadlines to be wirelessly charged associated with the plurality of medical devices.

Example 27. The charging device of example 26, wherein the processing circuitry is further configured to: determine that the charging device is unable to meet one or more of the deadlines to be wirelessly charged associated with a second one or more of the plurality of medical devices; and in response to determining that the charging device is unable to meet the one or more of the deadlines to be wirelessly charged associated with the second one or more of the plurality of medical devices, delegate wireless charging of the second one or more of the plurality of medical devices to one or more other charging devices.

Example 28. The charging device of any of examples 15-27, wherein the processing circuitry is further configured to: prior to wirelessly transmitting power to the medical device, broadcast, via the communication circuitry, an indication the charging device is about to wirelessly transmit power to the medical device to enable one or more other medical devices within wireless charging range of the charging device to turn off respective power receiving circuitry of each of the one or more other medical devices.

Example 29. An apparatus comprising means for performing any of the methods of examples 1-14.

Example 30. A non-transitory computer-readable storage medium comprising program instructions that, when executed by processing circuitry of a charging device, cause the processing circuitry to perform the methods of any of examples 1-14.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A method comprising:
   receiving, by processing circuitry of a charging device, a request to wirelessly charge a medical device;
   in response to receiving the request, physically moving, by the charging device, within wireless charging range of the medical device; and
   in response to determining that the charging device is within the wireless charging range of the medical device,
   prior to wirelessly transmitting power to the medical device, wirelessly broadcasting, by the processing circuitry and to the medical device and one or more other medical devices within wireless charging range of the charging device, a signal that indicates the medical device to which the charging device is about to wirelessly transmit power, and wirelessly transmitting, by power transmission circuitry of the charging device, power to the medical device to wirelessly charge the medical device.

2. The method of claim 1, wherein physically moving within wireless charging range of the medical device further comprises:

determining, by the processing circuitry, a location of the medical device; and physically moving, by the charging device, to the location of the medical device.

3. The method of claim 2, wherein the location of the medical device comprises Global Positioning System (GPS) information.

4. The method of claim 2, wherein the location of the medical device comprises a room of a facility.

5. The method of claim 2, wherein physically moving to the location of the medical device further comprises:

navigating, by the charging device using a floor plan of a facility, the facility to reach the location of the medical device.

6. The method of claim 1, further comprising:

establishing, by the processing circuitry, a secure communication session with the medical device;

receiving, by the processing circuitry from the medical device, one or more parameters associated with wirelessly charging the medical device; and configuring, by the processing circuitry, the power transmission circuitry of the charging device to wirelessly transmit power to the medical device according to the one or more parameters.

7. The method of claim 1, wherein receiving the request to wirelessly charge medical device further comprises receiving, by the processing circuitry, a plurality of requests to wirelessly charge a plurality of medical devices including the medical device, further comprising:

determining, by the processing circuitry, a prioritization of the plurality of medical devices; and wirelessly charging, by the power transmission circuitry, one or more of the plurality of medical devices based at least in part on the prioritization of the plurality of medical devices.

8. The method of claim 7, wherein determining the prioritization of the plurality of the medical devices further comprises:

determining, by the processing circuitry, deadlines to be wirelessly charged associated with the plurality of medical devices; and determining, by the processing circuitry, the prioritization of the plurality of medical devices based at least in part on the deadlines to be wirelessly charged associated with the plurality of medical devices.

9. The method of claim 8, further comprising:

determining, by the processing circuitry, that the charging device is unable to meet one or more of the deadlines to be wirelessly charged associated with a second one or more of the plurality of medical devices; and in response to determining that the charging device is unable to meet the one or more of the deadlines to be wirelessly charged associated with the second one or more of the plurality of medical devices, delegating, by the processing circuitry, wireless charging of the second one or more of the plurality of medical devices to one or more other charging devices.

10. The method of claim 1, wherein the signal that indicates the medical device to which the charging device is about to wirelessly transmit power causes the one or more other medical devices to turn off respective power receiving circuitry of each of the one or more other medical devices.

11. A charging device configured to wirelessly transmit power, wherein the charging device comprises:

movement mechanism configured to physically move the charging device;

communication circuitry configured for wireless communication;

power transmission circuitry configured to wirelessly transmit power; and processing circuitry electrically coupled to the movement mechanism, the communication circuitry, and the power transmission circuitry, wherein the processing circuitry is configured to:

receive, via the communication circuitry, a request to wirelessly charge a medical device; and in response to receiving the request, cause the movement mechanism to physically move the charging device within wireless charging range of the medical device;

wherein the power transmission circuitry is further configured to, in response to determining that the charging device is within the wireless charging range of the medical device, prior to wirelessly transmitting power to the medical device, wirelessly broadcast, to the medical device and one or more other medical devices within wireless charging range of the charging device, a signal that indicates the medical device to which the charging device is about to wirelessly transmit power, and wirelessly transmit power to the medical device to wirelessly charge the medical device.

12. The charging device of claim 11, wherein:

the processing circuitry is further configured to determine a location of the medical device; and to physically move the charging device within wireless charging range of the medical device, the movement mechanism is further configured to physically move the charging device to the location of the medical device.

13. The charging device of claim 12, wherein the location of the medical device comprises Global Positioning System (GPS) information.

14. The charging device of claim 12, wherein the location of the medical device comprises a room of a facility.

15. The charging device of claim 12, wherein processing circuitry is further configured to:

navigate a facility using a floor plan of the facility, the facility to cause the movement mechanism to physically move the charging device to reach the location of the medical device.

16. The charging device of claim 11, wherein the processing circuitry is further configured to:

establish, via the communication circuitry, a secure communication session with the medical device;

receive, via the communication circuitry and from the medical device, one or more parameters associated with wirelessly charging the medical device; and configure the power transmission circuitry of the charging device to wirelessly transmit power to the medical device according to the one or more parameters.

17. The charging device of claim 11, wherein to receive the request to wirelessly charge the medical device, the processing circuitry is further configured to:
- receive, via communication circuitry, a plurality of requests to wirelessly charge a plurality of medical devices including the medical device, further comprising:
- determine a prioritization of the plurality of medical devices; and
- cause the power transmission circuitry to wirelessly charge one or more of the plurality of medical devices based at least in part on the prioritization of the plurality of medical devices.

18. The charging device of claim 17, wherein to determine the prioritization of the plurality of medical devices, the processing circuitry is further configured to:
- determine deadlines to be wirelessly charged associated with the plurality of medical devices; and
- determine the prioritization of the plurality of medical devices based at least in part on the deadlines to be wirelessly charged associated with the plurality of medical devices.

19. The charging device of claim 18, wherein the processing circuitry is further configured to:
- determine that the charging device is unable to meet one or more of the deadlines to be wirelessly charged associated with a second one or more of the plurality of medical devices; and
- in response to determining that the charging device is unable to meet the one or more of the deadlines to be wirelessly charged associated with the second one or more of the plurality of medical devices, delegate wireless charging of the second one or more of the plurality of medical devices to one or more other charging devices.

20. A non-transitory computer-readable storage medium comprising program instructions that, when executed by processing circuitry of a charging device, cause the processing circuitry to:
- receive a request to wirelessly charge a medical device;
- in response to receiving the request, physically move within wireless charging range of the medical device; and
- in response to determining that the charging device is within the wireless charging range of the medical device,
  - prior to wirelessly transmitting power to the medical device, wirelessly broadcast, to the medical device and one or more other medical devices within wireless charging range of the charging device, a signal that indicates the medical device to which the charging device is about to wirelessly transmit power, and
  - wirelessly transmit, via power transmission circuitry of the charging device, power to the medical device to wirelessly charge the medical device.

* * * * *